(12) United States Patent
Tyagi et al.

(10) Patent No.: US 8,247,568 B2
(45) Date of Patent: Aug. 21, 2012

(54) PROCESS FOR THE PREPARATION OF PURE RABEPRAZOLE

(75) Inventors: Om Dutt Tyagi, Hyderabad (IN); Purna Chandra Ray, Hyderabad (IN); Madhuresh Kumar Sethi, Hyderabad (IN); Bhausaheb Chavhan, Hyderabad (IN)

(73) Assignee: Matrix Laboratories Ltd (IN)

( * ) Notice: Subject to any disclaimer, the term of this patent is extended or adjusted under 35 U.S.C. 154(b) by 342 days.

(21) Appl. No.: 12/665,851

(22) PCT Filed: Jun. 19, 2008

(86) PCT No.: PCT/IN2008/000388
§ 371 (c)(1),
(2), (4) Date: Dec. 21, 2009

(87) PCT Pub. No.: WO2008/155780
PCT Pub. Date: Dec. 24, 2008

(65) Prior Publication Data
US 2010/0190989 A1  Jul. 29, 2010

(30) Foreign Application Priority Data
Jun. 21, 2007 (IN) .............................. 1281/CHE/07

(51) Int. Cl.
*C07D 401/12* (2006.01)
(52) U.S. Cl. .................................................. 546/273.7
(58) Field of Classification Search ................ 546/273.7
See application file for complete search history.

(56) References Cited

U.S. PATENT DOCUMENTS

| 5,045,552 | A | 9/1991 | Souda et al. |
| 6,180,652 | B1 | 1/2001 | Tsujii et al. |
| 6,919,459 | B2 | 7/2005 | Broeckx et al. |

FOREIGN PATENT DOCUMENTS

| JP | 2001039975 A | 2/2001 |
| WO | 03101452 A1 | 12/2003 |
| WO | 2006117802 A2 | 11/2006 |
| WO | 2006120701 A1 | 11/2006 |

*Primary Examiner* — Patricia Morris
(74) *Attorney, Agent, or Firm* — Lerner, David, Littenberg, Krumholz & Mentlik, LLP

(57) ABSTRACT

The present invention relates to a process for the preparation of pure Rabeprazole sulfoxide using the solvent mixture for the extraction steps and this invention further relates to the process for the preparation of amorphous Rabeprazole sodium using pure rabeprazole base in presence of aqueous NaOH and water miscible solvent and adding an anti-solvent.

21 Claims, 4 Drawing Sheets

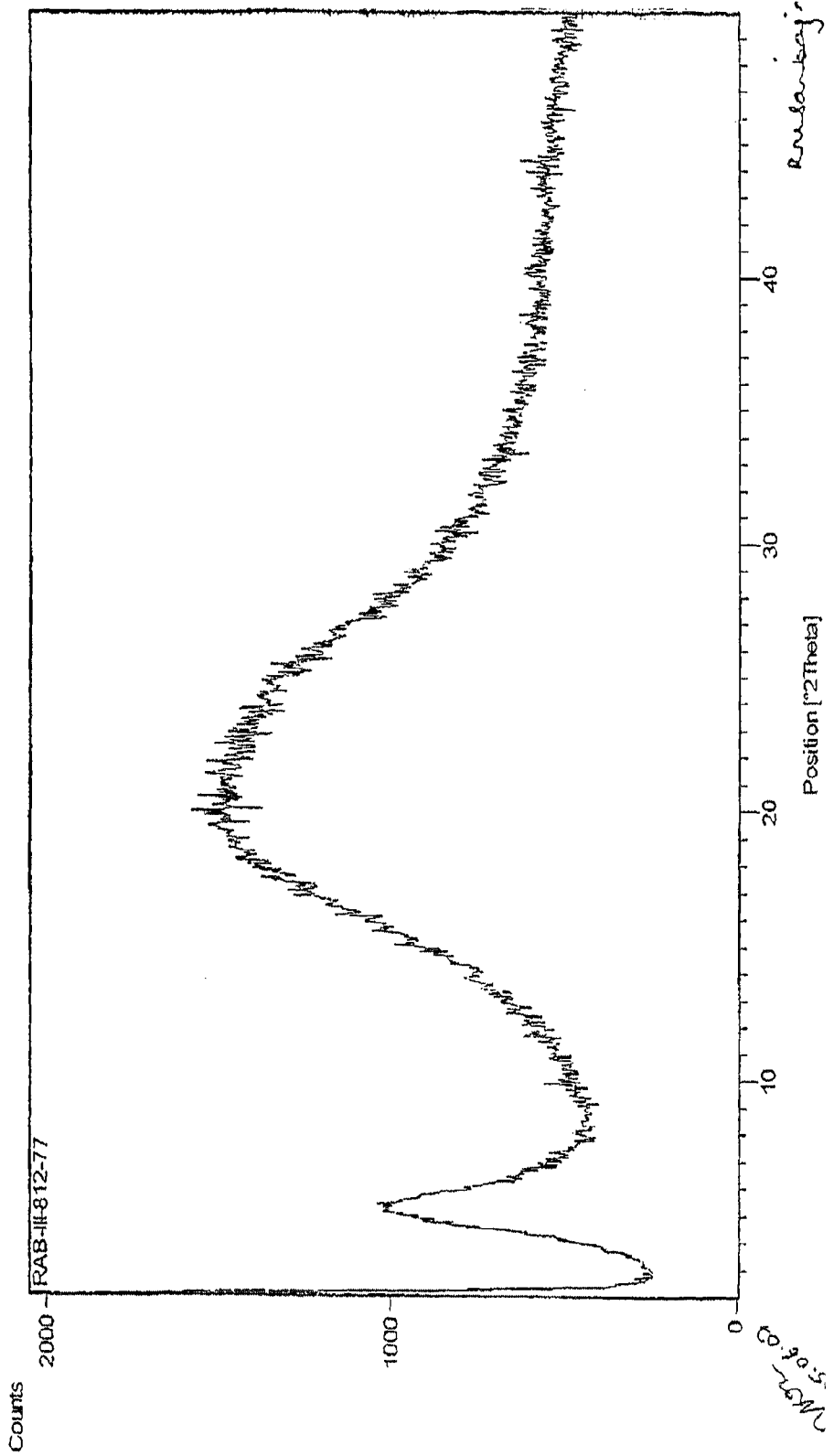

PROCESS FOR THE PREPARATION OF PURE RABEPRAZOLE

CROSS REFERENCE TO RELATED APPLICATIONS

The present application is a national phase entry under 35U.S.C. §371 of International Application No. PCT/IN2008/000388, filed 19 Jun. 2008, published in English, which claims the benefit of Indian Patent Application No. 1281/CHE/07, filed 21 Jun. 2007. The disclosures of said applications are incorporated by reference herein.

FIELD OF THE INVENTION

The present invention discloses efficient processes for the preparation of pure Rabeprazole and further relates to a novel process for the preparation of amorphous rabeprazole sodium.

BACKGROUND OF THE INVENTION

Rabeprazole, 2-[[[4-(3-Methoxypropoxy)-3-methyl-2-pyridinyl]methyl]sulfinyl]-1H-benzimidazole has the following structural formula

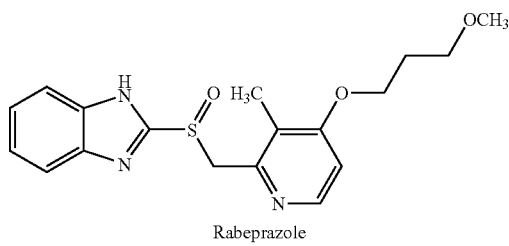

Rabeprazole

Rabeprazole belongs to a class of antisecretory compounds (substituted benzimidazole proton-pump inhibitors) that do not exhibit anticholinergic or histamine $H_2$-receptor antagonist properties, but suppress gastric acid secretion by inhibiting the gastric $H^+$, $K^+$ ATPase at the secretory surface of the gastric parietal cell. Because this enzyme is regarded as the acid (proton) pump within the parietal cell, rabeprazole has been characterized as a gastric proton-pump inhibitor. Rabeprazole blocks the final step of gastric acid secretion. So that it can effectively inhibit the secretion of an acid and is therefore effective in the therapy or prevention of human and animal peptic ulcer.

The U.S. Pat. No. 5,045,552 discloses the Rabeprazole and many other substituted benzimidazole-type compounds having anti-ulcer activity. This patent further discloses the process for preparation of Rabeprazole by oxidation of Rabeprazole sulfide using 85% m-chloroperbenzoic acid in a mixture of dichloromethane and diethyl ether followed by work up to get product as oil. The obtained oil is crystallized from a mixture of dichloromethane/ether. Optionally the oily crude is dissolved in aqueous solution of sodium hydroxide. The obtained solution is subjected to azeotropic distillation with ethanol to remove water and adding ether to get crystalline Rabeprazole base.

Scheme-I

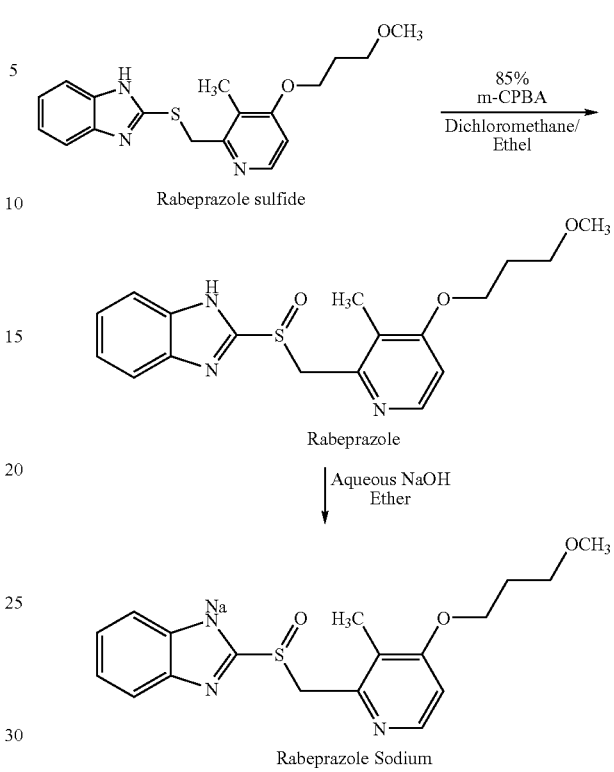

According to the prior art, Rabeprazole base is crystallized using dichloromethane/ether to obtain crystalline off white product. The HPLC purity is less than or equal to 99% and the isolation procedure involves azeotropic distillation of water, during which the product is exposed to high temperature and leads to certain impurities. Repeated crystallization is needed to remove impurities to get desired quality. Using large volumes of chlorinated solvents in the plant leads to environmental hazardous.

Japanese patent application JP2001039975 teaches that the product obtained by example 33 of U.S. Pat. No. 5,045,552 with a melting range of 140-141° C. corresponds to amorphous rabeprazole sodium The U.S. Pat. No. 6,919,459 patent also discloses the process for the preparation of Rabeprazole by oxidation of Rabeprazole sulfide using m-Chloroperbenzoic acid (m-CPBA) in a suitable solvent. The reaction mass is subjected to repeated washings at different pH levels and isolate the product from aqueous layer.

Scheme-II

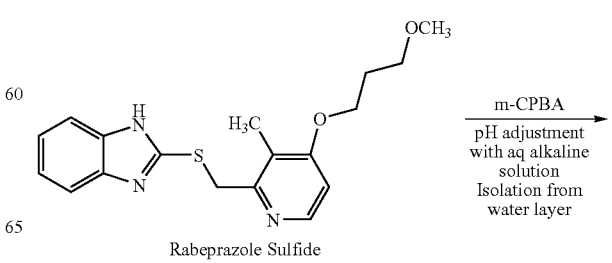

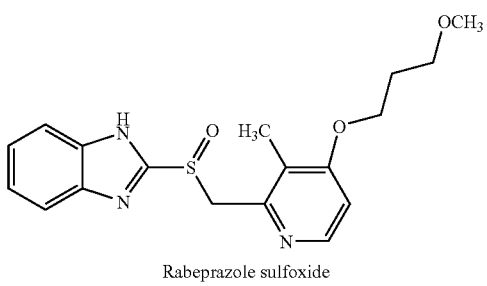

Rabeprazole sulfoxide

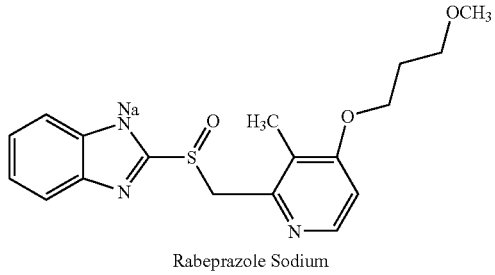

Rabeprazole Sodium

Rabeprazole is not stable at acidic conditions and decomposes to form unknown impurities. To remove these impurities repeated crystallizations are required to get desire quality of the final product.

The WO2006/117802 PCT application discloses the process for the preparation of Rabeprazole sodium by oxidation of Rabeprazole sulfide with sodium hypo halite solution in water or a mixture of water and water miscible solvent medium using alkali metal hydroxide and catalyst. The reaction mass is saturated by inorganic saturating agents and the Rabeprazole sodium salt is extracted with water immiscible organic solvent. Organic solvent is distilled and the residue is dissolved in second organic solvent to get clear solution, which is precipitated by adding antisolvent.

The WO2006/120701 PCT application discloses process for manufacture of amorphous Rabeprazole sodium by the reaction of Rabeprazole base with aqueous sodium hydroxide. Ethanol is added to the obtained solution. Solvents are distilled from the solution to get thick mass. Organic solvent is added to the obtained residue to get clear solution, to which antisolvent is added to get amorphous Rabeprazole sodium.

The prior art methods cited above have many disadvantages, these methods involve more number of organic solvents and lack successive extractions and washings of the layers during work up procedure. It leads to many impurities that ultimately affect on purity and yield loss of final product.

The U.S. Pat. No. 6,180,652 and WO 2003101452 PCT application discloses the process for the preparation of amorphous rabeprazole sodium, which is obtained by lyophilization of an aqueous solution of rabeprazole sodium acetone complex and an aqueous NaOH solution of Rabeprazole respectively.

Scheme-III

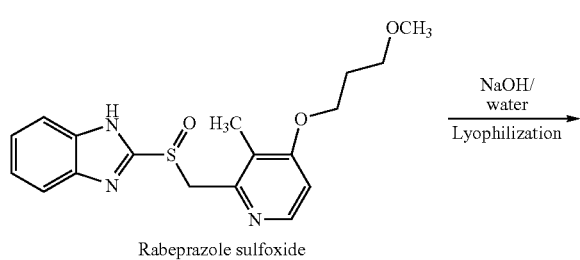

Rabeprazole sulfoxide

NaOH/water
Lyophilization

Lyophilization technique is not suitable for production at industrial scale and it needs more time cycle and involves the cost.

We observed that rabeprazole is rapidly degraded in chlorinated solvent like dichloromethane to form unknown impurities, due to impurities while distillation gummy material is formed. It leads to yellowish color in final product, finally it leads to yield loss in final product.

According to prior art methods,
(a) Dichloromethane/ether is used for final crystallization gives off white product with HPLC purity less than or equal to 99% and
(b) Rabeprazole sodium is isolated by using azeotropic distillation. It needs high temperature to remove water and the reaction mass is exposed to high temperature to form unknown impurities, to remove these impurities repeated crystallizations are required to get desire quality of the final product.

To overcome all above problems there is a need to develop such a process which is plant friendly and gives extra pure and white colored Rabeprazole base and subsequent sodium salt

OBJECT OF THE INVENTION

The main object of the present invention is to provide the amorphous rabeprazole sodium.

Another object of the present invention is to provide pure Rabeprazole base using solvent mixture for extraction step to prevent degradation of Rabeprazole base, which gives amorphous Rabeprazole sodium.

Yet another object of this invention is to provide Rabeprazole base having HPLC purity more than 99.5% with good description.

Yet to another object of the invention is to provide a novel process for the preparation of amorphous Rabeprazole sodium in presence of aqueous NaOH in water miscible organic solvent and adding anti-solvent by using pure Rabeprazole base.

SUMMARY OF THE INVENTION

The present invention relates to a process for the preparation of amorphous rabeprazole sodium comprising reaction of pure rabeprazole base with aqueous sodium hydroxide in water miscible organic solvent followed by removal of solvent and addition of antisolvent.

The invention also relates to a process for the preparation of pure Rabeprazole base from rabeprazole sulfide by oxidation and workup procedure involving extractions using solvent mixture and crystallization of crude rabeprazole base from alcohol and antisolvent.

DETAILED DESCRIPTION OF THE INVENTION

Figure 1:
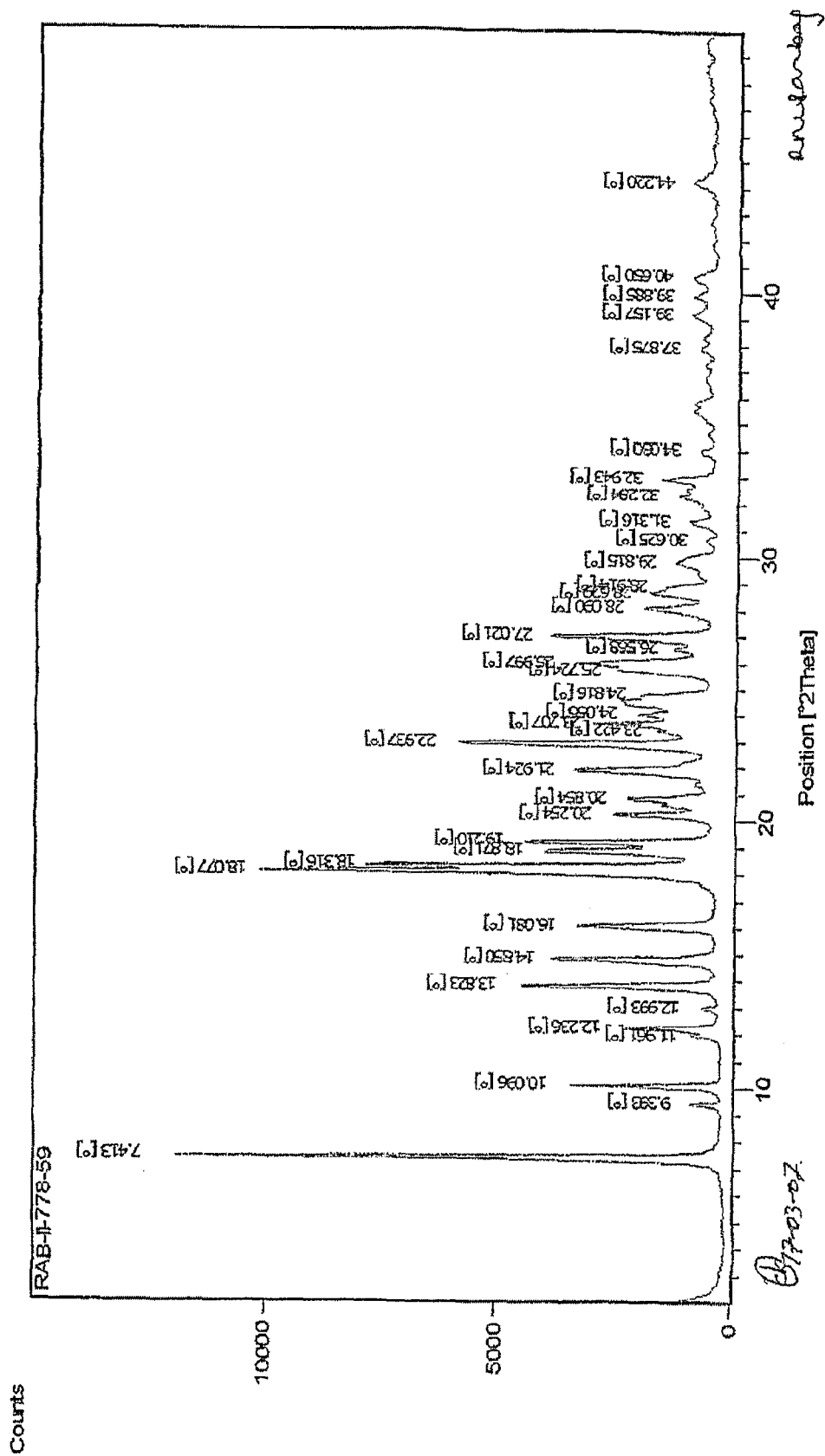
FIG. 1—shows the X-ray diffractogram pattern of crystalline Rabeprazole base of product patent FIG. 2—shows the X-ray diffractogram pattern of crystalline Rabeprazole base of present invention FIG. 3—shows the x-ray diffractogram pattern of amorphous sodium rabeprazole sodium of product patent FIG. 4—shows the x-ray diffractogram pattern of amorphous rabeprazole sodium obtained according to the present invention
Figure 2:
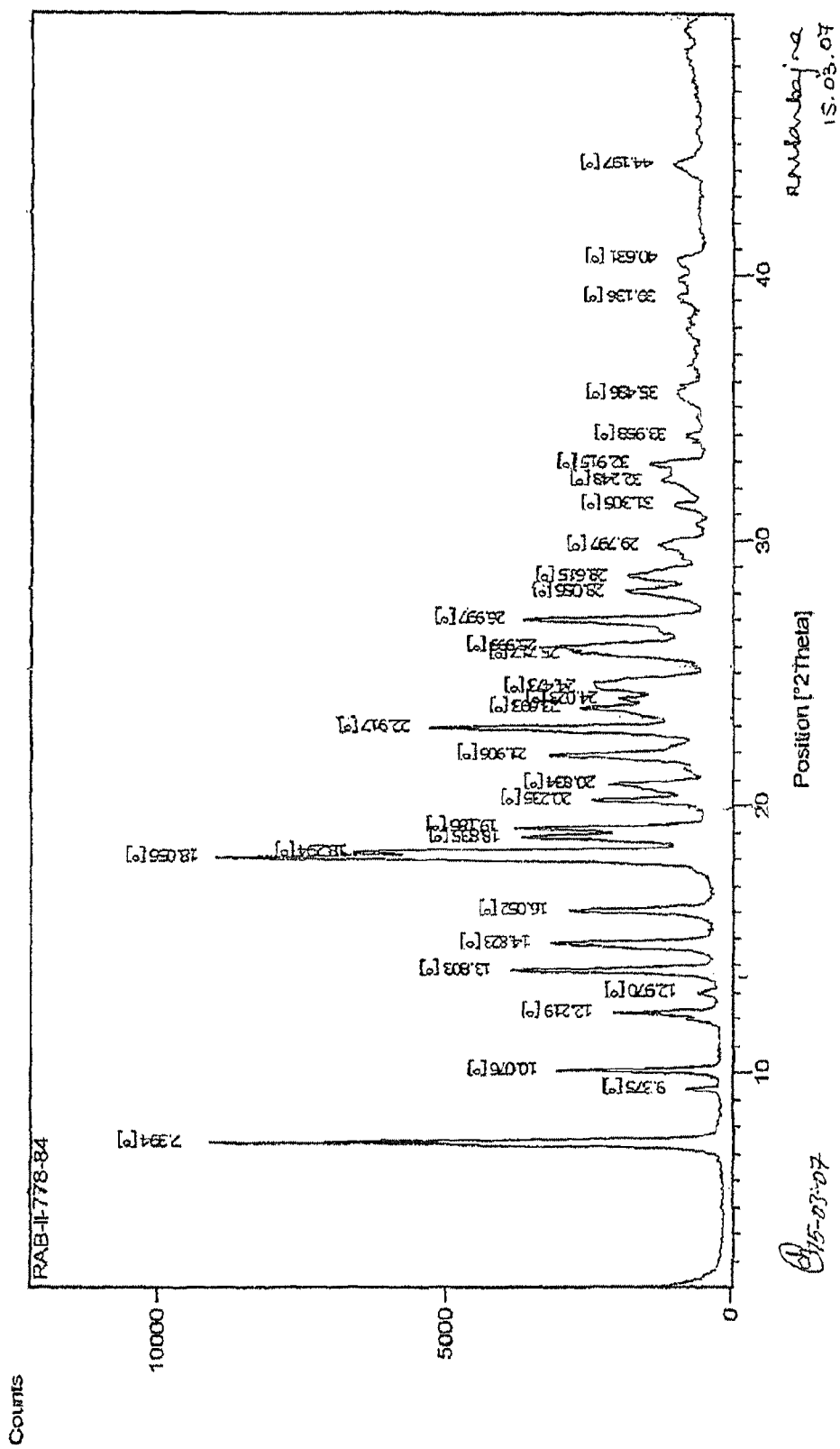
Figure 3:
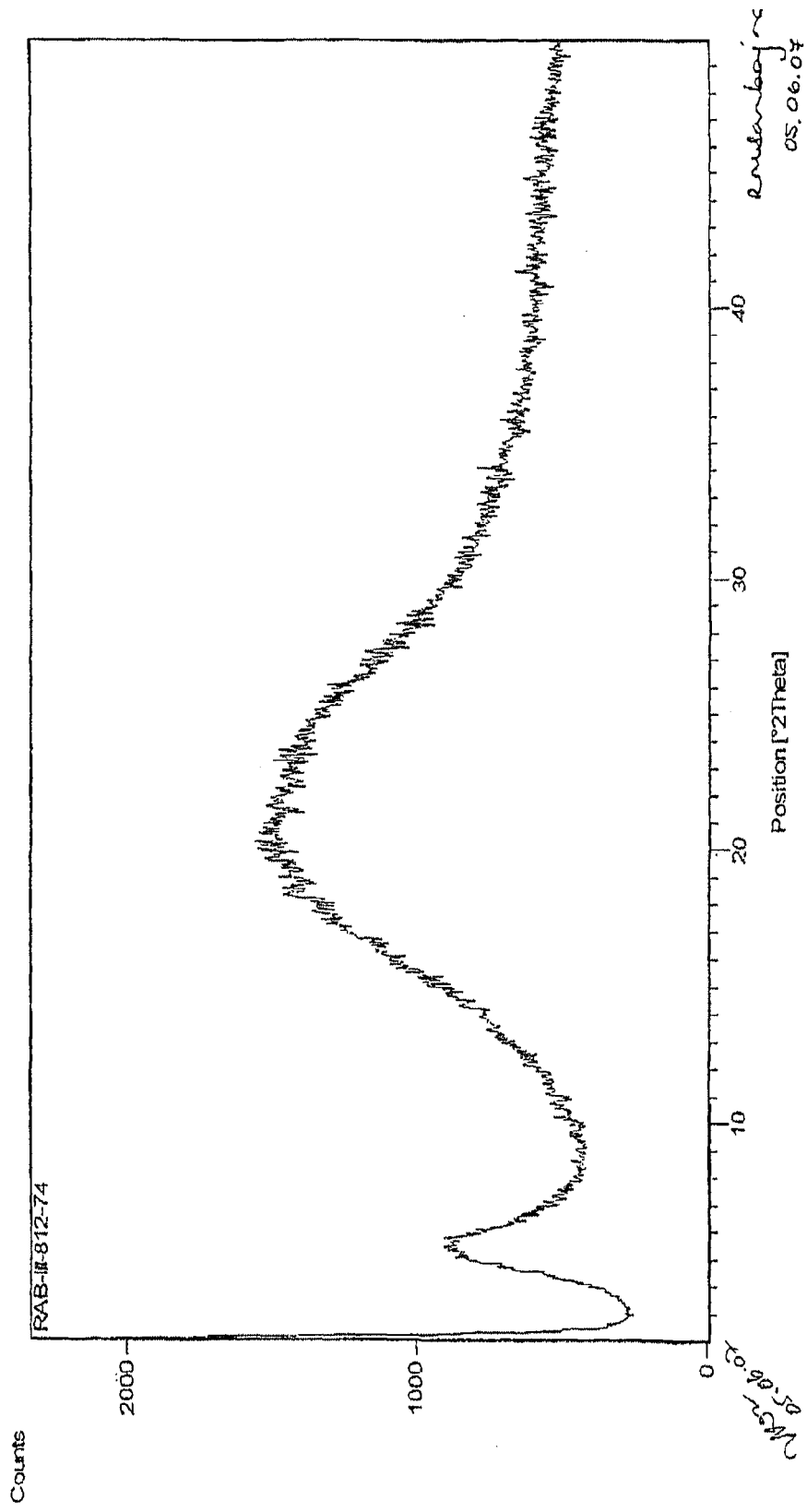

Thus in accordance with the present invention is achieved by a process for the preparation of amorphous Rabeprazole sodium from pure rabeprazole base, the said process comprising the steps of:
a) suspending Rabeprazole base in water miscible organic solvent,
b) adding aqueous sodium hydroxide,
c) removing the solvent,
d) dissolving the residue from step c in water miscible organic solvent,
e) adding anti-solvent and
f) isolating amorphous Rabeprazole sodium.

According to the present invention, rabeprazole base is suspended in water miscible organic solvent selected from tetrahydrofuran, acetone, acetonitrile and $C_1$-$C_4$ alcohols such as methanol, ethanol and mixtures there of. Aqueous sodium hydroxide is added to the obtained suspension temperature between 10-50° C., preferred temperature is at 25-30° C.

The solvent is removed by distillation under reduced pressure below 35° C. completely. Residue is dissolved in above said water miscible organic solvent to get solution and antisolvent is added temperature between 10-50° C., preferred temperature is at 25-30° C. The antisolvent used is selected from diisopropyl ether, diethyl ether, methyl tent-butyl ether, n-pentane, n-hexane, n-heptane, cyclohexane and mixtures thereof. The product is filtered and it is dried at 50° C. under vacuum to obtain amorphous rabeprazole sodium.

The prepared Rabeprazole sodium according to the present invention, is identified as amorphous form by the characteristic melting range, DSC and XRD Scheme-IV

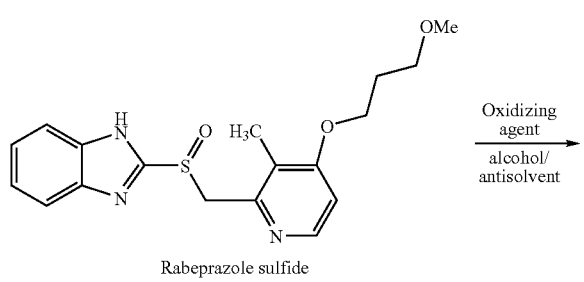

Rabeprazole sulfide

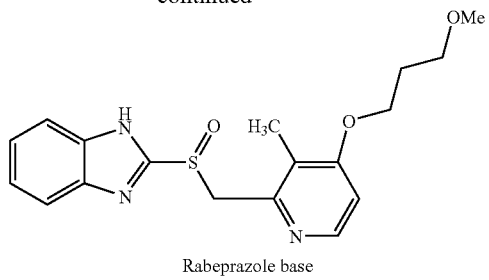

Rabeprazole base

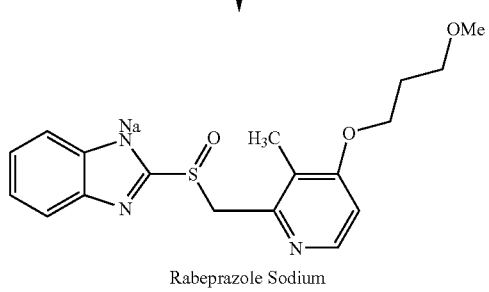

Rabeprazole Sodium

Another aspect of the present invention is to provide a process for the preparation of pure rabeprazole base comprising the following steps:
a) dissolving rabeprazole sulfide in a solvent medium
b) treating with oxidizing agent in the presence of base
c) adjusting the pH with base above 12.0
d) washing the resulting solution of step c with solvent mixture and separating the organic layer
e) adjusting the aqueous layer pH with salt extracting the aqueous layer with solvent mixture at a pH ranging between 9.0 to 11.0, separating the aqueous layer
g) removing the solvent to get residue
h) dissolving residue in alcohol
i) precipitating by adding an anti solvent and
j) isolating the pure rabeprazole base Oxidation of Raberapzole sulfide is carried out with oxidizing agents selected from hypohalites such as sodium hypochlorite and sodium hypobromite in presence of base selected from alkali and alkali earth hydroxides preferably sodium hydroxide, potassium hydroxide and calcium hydroxide in solvent medium, which is selected from water miscible alcohols preferably methanol, ethanol at a temperature ranging from −15 to −25° C., preferred temperature is.

After completion the reaction, sodium thiosulphate solution is added to the reaction mass at 10° C. Reaction mass pH is adjusted to above 12.0 preferably 12.8 to 13.5 using caustic solution. The resulting solution is washed with solvent mixture selected from a mixture of chlorinated solvent and polar aprotic solvent and the organic layer is separated. The chlorinated solvent used is selected from dichloromethane, chloroform, carbon tetrachloride and said polar aprotic solvent is selected from dimethyl acetamide, dimethyl formamide and dimethyl sulfoxide. The organic washing is re extracted with water, combined aqueous layer pH is adjusted with a salt selected from ammonium salts such as ammonium chloride and ammonium sulfate, preferably ammonium chloride. The adjusted pH is ranging from 9.0 to 11.0 at which the aqueous layer is extracted with above said solvent mixture and the aqueous layer is separated. Solvent is removed from the organic layer to get the rabeprazole base residue.

The above obtained rabeprazole base residue is dissolved in alcohol preferably C1-C4 alcohols such as methanol, ethanol, isopropanol, n-butanol and tertiary butanol to get the clear solution. The resulting clear solution is precipitated by addition of anti solvent selected from diisopropyl ether, diethyl ether and methyl tert-butyl ether. The slurry is filtered, washed with ether and dried at 40-45° C. under vacuum to get pure crystalline rabeprazole base.

The invention is further illustrated with non-limiting examples

Example-1

Preparation of 2-[[[4-(3-methoxypropoxy)-3-methyl-2-pyridinyl]methyl]sulfinyl]-1H-benzimidazole (Rabeprazole base)

To a solution of 2-[[4-(3-Methoxypropxy)-3-methylpyridine-2-yl]-2-methylthio]-1H-bezamidazole (Rabeprazole sulfide) (25 g) in methanol (125 ml), added sodium hydroxide solution (1.5N, 200 ml). Reaction mass Was cooled to −15 to −25° C. under stirring. A solution of sodium hypochlorite (~1%, 550 ml) was added slowly at −15 to −25° C. to the reaction mass over a period of 45-75 minutes. The progress of reaction was monitored by HPLC. After completion of reaction, added solution of sodium thiosulphate and gradually raised the temperature to 10° C. in 20-30 minutes. The pH of reaction mass was adjusted to 12.8 to 13.5 using caustic solution (~50 ml) and mixture of methylene chloride (125 ml) & dimethyl acetamide (1.25 ml) was added at room temperature and stirred for 15 minutes. Separated the two layers & kept methylene chloride layer aside. Again washed the aqueous layer with methylene chloride (75 ml) & dimethyl acetamide (1 ml) and separated the aqueous layer. Combined both methylene chloride layers and extracted with water (2×125 ml). The pH of combined aqueous layer was adjusted to 9.4-9.8 with saturated solution of ammonium chloride. Aqueous layer was extracted using methylene chloride (125 ml) & dimethyl acetamide (1 ml) followed by further extraction using a mixture of methylene chloride (75 ml) & dimethyl acetamide (1 ml). Combined both methylene chloride layers and washed with water (50 ml). The methylene chloride layer was treated with activated carbon and dried ($Na_2SO_4$). To the residue obtained after distillation of methylene chloride completely under reduced pressure, added methanol (25 ml) and stirred for 5-10 minutes. The obtained solution was precipitated with diisopropyl ether (350 ml). The reaction mass was stirred for 1-2 hours at 20-30° C. and filtered. The wet cake was washed with diisopropyl ether (2×25 ml) and the product was dried under vacuum at 40-45° C.

Dry weight=54 g.
HPLC purity=99.69%

Example-2

Preparation of Amorphous Rabeprazole Sodium

Rabeprazole (10 g) was suspended in 30 ml THF and sodium hydroxide solution (1.11 g sodium hydroxide dissolved in 1 ml water) was added at 25-30° C. Reaction mass was stirred for 30 minutes at 25-30° C. Added activated charcoal (1.0 g) and stirred for 30 minutes at 25-30° C. Filtered and washed charcoal bed with THF (20 ml). Distilled out THF under reduced pressure at 30-35° C. completely. Residue was dissolved in THF (20 ml). In a separate R B flask charged n-heptane (100 ml) at 25° C. Added slowly above reaction mass in 15-20 minutes at 25-30° C. Stirred at 25-30° C. for 2 hours. The product was filtered off under nitrogen atmosphere and wet cake was washed with n-heptane (2×20 ml). Dried under vacuum at 50° C. for 20-24 hours to obtain amorphous Rabeprazole sodium.

Dry wt.=9.2 gram
HPLC purity: 99.54%

Example-3

Preparation of Amorphous Rabeprazole Sodium

Rabeprazole (10 g) was suspended in 30 ml THF and added sodium hydroxide solution (1.11 g sodium hydroxide dissolved in 1 ml water) at 25-30° C. Reaction mass was stirred for 30 minutes at 25-30° C. Added activated charcoal (1.0 g) and stirred for 30 minutes at 25-30° C. Filter and washed charcoal bed with THF (20 ml). Distilled out THF under reduced pressure at 30-35° C. completely. Dissolved residue in THF (20 ml). In a separate R B flask charged diisopropyl ether (100 ml) at 25° C. Added slowly above reaction mass in 15-20 minutes at 25-30° C. Stirred at 25-30° C. for 2 hours. The product was filtered off under nitrogen atmosphere and wet cake was washed with diisopropyl ether (2×20 ml). Dried under vacuum at 50° C. for 20-24 hours to obtain amorphous Rabeprazole sodium.

Dry wt.=9.2 gram
HPLC purity: 99.41%

Example-4

Preparation of Amorphous Rabeprazole Sodium

Rabeprazole (10 g) was suspended in 20 ml water and sodium hydroxide solution (1.11 g sodium hydroxide dissolved in 10 ml water) was added at 25-30° C. Reaction mass was stirred for 30 minutes at 25-30° C. Added activated charcoal (1.0 g) and stirred for 30 minutes at 25-30° C. Filtered and washed charcoal bed with water (10 ml). Added 30 ml ethanol to filtrate and distilled out till get oily residue under reduced pressure at 30-35° C. Again added 30 ml ethanol to the oily residue and distilled out completely under reduced pressure at 35° C. To the residue added 100 ml diisopropyl ether and stirred at 25-30° C. for two hours. Filtered product under nitrogen atmosphere and washed with 20 ml diisopropyl ether. Dried under vacuum at 50° C. for 20-24 hours to obtain amorphous Rabeprazole sodium.

Dry wt.=9.4 gram
HPLC purity: 99.80%

The invention claimed is:

1. A process for the preparation of pure Rabeprazole base, which comprises the following steps:
    a) dissolving Rabeprazole sulfide in a solvent medium,
    b) treating with oxidizing agent in the presence of base,
    c) adjusting the pH with base above 12.0,
    d) washing resulting solution of step c with solvent mixture and separating the organic layer,
    e) adjusting the aqueous layer pH with salt,
    f) extracting the aqueous layer with solvent mixture at a pH ranging between 9.0 to 11.0, separating the aqueous layer,
    g) removing the solvent to get residue,
    h) dissolving residue in alcohol,
    i) precipitating by adding an anti solvent and
    j) isolating the Rabeprazole base.

2. The process according to claim 1, wherein solvent medium is selected from water miscible alcohols.

3. The process according to claim 2, wherein water miscible alcohols are selected from methanol, ethanol, isopropyl alcohol and tertiary butanol.

4. The process according to claim 1, wherein oxidizing agent is selected from hypohalites.

5. The process according to claim 4, wherein hypohalites is selected from sodium hypochlorite and sodium hypobromite.

6. The process according to claim 1, wherein base is selected from alkali metal and alkaline earth metal hydroxides.

7. The process according to claim 6, wherein alkali metal and alkaline earth metal hydroxides are selected from sodium hydroxide, potassium hydroxide and calcium hydroxide.

8. The process according to claim 1 step (d), wherein solvent mixture is selected from mixture of chlorinated solvent and polar aprotic solvent.

9. The process according to claim 8, wherein chlorinated solvent is selected from dichloromethane, chloroform and carbon tetrachloride.

10. The process according to claim 8, wherein polar aprotic solvent is selected from dimethyl acetamide, dimethyl formamide and dimethyl sulfoxide.

11. The process according to claim 1 step (e), wherein salt is selected from ammonium chloride and ammonium sulphate.

12. The process according to claim 1, wherein alcohol is selected from methanol, ethanol isopropanol, n-butanol and tertiary butanol.

13. The process according to claim 1, wherein antisolvent is selected from ethers.

14. The process according to claim 13, wherein ether is selected form diisopropyl ether, diethyl ether and methyl tert butyl ether.

15. The process according to claim 1 further comprising the step of converting the Rabeprazole base to a Rabeprazole sodium salt.

16. The process according to claim 15 wherein said converting comprises the following steps:
   a) suspending Rabeprazole base in water miscible solvent,
   b) adding aqueous sodium hydroxide,
   c) removing the solvent,
   d) adding anti-solvent and
   e) isolating Rabeprazole sodium.

17. The process of claim 16, wherein the water miscible solvent is selected from tetrahydrofuran, acetone, acetonitrile, methanol, ethanol, isopropyl alcohol and tert-butyl alcohol.

18. The process of claim 16, wherein the anti-solvent is selected from ethers and alkanes.

19. The process of claim 18, wherein the ether is selected from diisopropyl ether, diethyl ether and methyl tert butyl ether.

20. The process of claim 18, wherein the alkane is selected from n-pentane, n-hexane, n-heptane and cyclohexane.

21. The process of claim 16 wherein the Rabeprazole sodium is amorphous.

\* \* \* \* \*